United States Patent [19]

Kar et al.

[11] Patent Number: 5,099,055

[45] Date of Patent: Mar. 24, 1992

[54] (FLUORINATED PHENOXY)(3-PERFLUORO-ALKYL-PHENOXY)-CYCLIC PHOSPHAZENES

[75] Inventors: Kishore K. Kar, Midland; Chester E. Pawloski, Bay City, both of Mich.

[73] Assignee: The Dow Chemical Company, Midland, Mich.

[21] Appl. No.: 645,152

[22] Filed: Jan. 22, 1991

Related U.S. Application Data

[62] Division of Ser. No. 417,363, Oct. 5, 1989, Pat. No. 5,015,405.

[51] Int. Cl.$^5$ .................. C07F 9/6593; C07F 9/6581
[52] U.S. Cl. ........................................ 558/80
[58] Field of Search ............................ 558/80

[56] References Cited

U.S. PATENT DOCUMENTS

| | | | |
|---|---|---|---|
| 2,109,491 | 3/1938 | Lipkin | 87/9 |
| 2,192,921 | 3/1940 | Lipkin | 260/461 |
| 2,214,769 | 9/1940 | Lipkin | 260/2 |
| 2,876,247 | 3/1959 | Ratz et al. | 260/461 |
| 3,136,727 | 6/1964 | Nichols | 252/19.9 |
| 3,201,445 | 8/1965 | Drysdale et al. | 260/461 |
| 3,234,304 | 2/1966 | Nichols | 260/927 |
| 3,251,538 | 5/1966 | Barnitz | 230/101 |
| 3,280,222 | 10/1966 | Kober et al. | 260/927 |
| 3,291,865 | 12/1966 | Kober et al. | 260/927 |
| 3,313,731 | 4/1967 | Dolle et al. | 252/49.7 |
| 3,316,330 | 4/1967 | Nichols | 260/927 |
| 3,459,838 | 8/1969 | Klender | 260/973 |
| 4,029,634 | 6/1977 | Meredith | 260/45.9 NP |
| 4,600,791 | 7/1986 | Carr et al. | 558/80 |
| 4,601,843 | 7/1986 | Carr et al. | 252/78.5 |
| 4,698,439 | 10/1987 | Kolich et al. | 558/80 |
| 4,724,264 | 2/1988 | Nakacho et al. | 558/80 |
| 4,727,175 | 2/1988 | Bezoari | 558/80 |
| 4,727,176 | 2/1988 | Bezoari | 558/80 |

FOREIGN PATENT DOCUMENTS 0241877 10/1987 European Pat. Off. .

OTHER PUBLICATIONS

Derwent 86-344309/52 (JP 103543) (1986).
Derwent 87-046645/07 (JP145272) (1987).
Derwent 23211 K/10 (JP 111704) (1983).

*Primary Examiner*—Mary C. Lee
*Assistant Examiner*—Michael G. Ambrose

[57] ABSTRACT

Cyclic phosphazenes completely substituted with fluorinated phenoxy and m-perfluoroalkylphenoxy moieties in ratios ranging from about 1:1 to about 1:5 are disclosed. These compounds, either alone or as additives, are useful as high temperature lubricants.

15 Claims, No Drawings

(FLUORINATED PHENOXY)(3-PERFLUORO-ALKYLPHENOXY)-CYCLIC PHOSPHAZENES

CROSS-REFERENCE TO RELATED APPLICATION

This is a divisional of application Ser. No. 417,363, filed Oct. 5, 1989, now U.S. Pat. No. 5,015,405.

BACKGROUND OF THE INVENTION

The present invention is related to cyclic phosphazenes.

Various phosphazenes are known in the art. For example, U.S. Pat. Nos. 3,316,330 and 3,234,304 disclose cyclic compounds corresponding to the formula:

$$P_m N_m R_x R'_y R''_z \quad (I)$$

wherein R is m-trifluoromethoxyphenoxy, R' is phenoxy and R" is m-trifluoromethylphenoxy, m is an integer of from 3 to 7, x is at least one and the sum of x, y and z is 2 m. The materials are disclosed to be useful as high temperature lubricants, working fluids and plasticizers. Additional examples of other substituted phosphazenes are disclosed in U.S. Pat. No. 3,136,727; European Patent Application 0241877; U.S. Pat. No. 3,280,222 and U.S. Pat. No. 3,459,838. These phosphazenes are also generally taught to be useful as lubricants and working fluids.

The demands placed on these materials and other existing lubricants are currently undergoing significant changes. Engines are being developed for automotive and aeronautic applications that have requirements dramatically different from those of engines currently in use. It is anticipated that these engines will operate at temperatures exceeding 250° C. and will be constructed using materials new or different from those currently in use. Thus, what is needed are novel compounds useful as lubricants or lubricant additives that are stable at the high use temperatures while possessing the other properties required of lubricants.

SUMMARY OF THE INVENTION

The present invention is directed to oligomeric, preferably trimeric or tetrameric or mixtures thereof, cyclic phosphazenes substituted with fluorinated phenoxy moieties and 3-perfluoroalkylphenoxy moieties with the proviso that the ratio of fluorinated phenoxy to 3-perfluoroalkylphenoxy moieties on the phosphazene ring ranges from about 1:5 to about 1:1.

The compounds of the present invention are useful as extended temperature lubricants.

DETAILED DESCRIPTION OF THE ILLUSTRATIVE EMBODIMENTS

The cyclic phosphazenes of the present invention are preferably trimeric although higher oligomers such as tetramers may be used. When the trimeric oligomers are used, they may contain minor amounts of highers.

The cyclic phosphazenes preferably correspond to the formula:

$$\left[ N=P \begin{array}{c} (R)_2 \\ | \end{array} \right]_n \quad (II)$$

wherein n is 3 through 7, R is individually in each occurrence fluorinated phenoxy or 3-perfluoroalkylphenoxy with the proviso that the ratio of fluorinated phenoxy to 3-perfluoroalkylphenoxy ranges from about 1:5 to about 1:1.

The fluorinated phenoxy moieties contain from one to five fluorine atoms. It is preferred that the fluorinated phenoxy moiety contain one fluorine atom and that the fluorine atom is meta or para to the oxygen atom of the phenoxy moiety. The perfluoroalkyl group of the meta-perfluoroalkylphenoxy is preferably a lower perfluoroalkyl group having from one to about five carbon atoms and is most preferably a trifluoromethyl group.

The ratio of fluorinated phenoxy to perfluoroalkylphenoxy substituents ranges from about 1:5 to about 1:1. It is preferred that the ratio ranges from about 1:2 to about 1:1. It is more preferred that the ratio is about 1:2. While the compounds of the present invention are described as single molecules having specified substituents present in a stated ratio, it will be realized by one skilled in the art that the compounds will exist as statistical mixtures of molecules. Some of these molecules will have the specified ratio of substituents while others will have higher or lower ratios. However, the phosphazenes will, within these statistical mixtures, have substituents present at the specified ratios.

Non-limiting examples of the cyclic phosphazenes of this invention thus include 2,2,4,4,6,6-di(4-fluorophenoxy)tetra(3-trifluoromethylphenoxy)-1,3,5-triaza-2,4,6-triphosphorine, 2,2,4,4,6,6-di(3-fluorophenoxy)tetra(3-trifluoromethylphenoxy)-1,3,5-triaza-2,4,6-triphosphorine, 2,2,4,4,6,6-di(2-fluorophenoxy)tetra(3-trifluoromethylphenoxy)-1,3,5-triaza-2,4,6-triphosphorine, 2,2,4,4,6,6-tri(2-fluorophenoxy)tri(3-trifluoromethylphenoxy)-1,3,5-triaza-2,4,6-triphosphorine, 2,2,4,4,6,6-tri(3-fluorophenoxy)tri(3-trifluoromethylphenoxy)-1,3,5-triaza-2,4,6-triphosphorine, 2,2,4,4,6,6-tri(4-fluorophenoxy)tri(3-trifluoromethylphenoxy)-1,3,5-triaza-2,4,6-triphosphorine, 2,2,4,4,6,6,8,8-tri(4-fluorophenoxy)penta(3-trifluoromethylphenoxy)-1,3,5,7-tetraza-2,4,6,8-tetraphosphorine, 2,2,4,4,6,6,8,8-tri(3-fluorophenoxy)penta(3-trifluoromethylphenoxy)-1,3,5,7-tetraza-2,4,6,8-tetraphosphorine, 2,2,4,4,6,6,8,8-tetra(4-fluorophenoxy)tetra(3-trifluoromethylphenoxy)-1,3,5,7-tetraza-2,4,6,8-tetraphosphorine, 2,2,4,4,6,6,8,8-tetra(3-fluorophenoxy)tetra(3-trifluoromethylphenoxy)-1,3,5,7-tetraza-2,4,6,8-tetraphosphorine, 2,2,4,4,6,6,8,8-2.57(3-fluorophenoxy)-5.43(3-trifluoromethylphenoxy)-1,3,5,7-tetraza-2,4,6,8-tetraphosphorine, 2,2,4,4,6,6,8,8-2.57(4-fluorophenoxy)-5.43(3-trifluoromethylphenoxy)-1,3,5,7-tetraza-2,4,6,8-tetraphosphorine and mixtures thereof. In a preferred embodiment, the phosphazene is 2,2,4,4,6,6-di(3-fluorophenoxy)tetra(m-trifluoromethylphenoxy)-1,3,5-triaza-2,4,6-triphosphorine, 2,2,4,4,6,6-di(4-fluorophenoxy)tetra(m-trifluoromethylphenoxy)-1,3,5-triaza-2,4,6-triphosphorine or mixtures thereof.

The compounds of this invention may be prepared by methods known in the art. It is preferred that they are prepared in a one-pot, two-stage reaction. In the first stage, a fluorinated phenol and a perfluoroalkylphenol are placed into a flask with a solvent. An alkali metal hydroxide is added and the mixture is allowed to reflux and the waters of reaction are removed. The mixture is then allowed to cool and a halogenated cyclic phosphazene is added and the mixture is refluxed. The product is then recovered using conventional techniques. The fluorinated phenol, perfluoroalkylphenol and halogenated phosphazene starting materials are commercially available or may be prepared using conventional techniques.

In the preparation of the compounds of this invention, the fluorinated phenol, the perfluoroalkylphenol and the halogenated phosphazene reactants are used in amounts sufficient to insure that the fluorinated phenol and perfluoroalkylphenol are present in a ratio of from about 1:1 to about 1:2 and the fluorinated phenol and perfluoroalkylphenol completely replace the halogens on the phosphazene ring. For example, when the phosphazene is a trimer such as 2,2,4,4,6,6-hexachloro-1,3,5-triaza-2,4,6-triphosphorine, it is preferred to use at least about two moles of fluorinated phenol and at least about four moles of perfluoroalkylphenol per mole of 2,2,4,4,6,6-hexachloro-1,3,5-triaza-2,4,6-triphosphorine. When the phosphazene is a tetramer, it is preferred to use at least about 2.6 moles of fluorinated phenol and at least about 5.4 moles of perfluoroalkylphenol per mole of 2,2,4,4,6,6,8,8-octachloro-1,3,5,7-tetraza-2,4,6,8-tetraphosphorine. It is preferred to use a slight stoichiometric excess each of fluorinated phenol and perfluoroalkylphenol to insure complete reaction.

The compounds of this invention are useful as lubricants over extended temperature ranges. They may be used alone and also may be used in conjunction with various additives to improve their performance. Additionally, they may themselves be used as additives with other base stocks.

When used as an additive to a base stock, the phosphazenes of the present invention must be compatible with the base stock. By compatible, it is meant that the phosphazenes of the present invention may be readily dispersed or dissolved in the base stock, either with or without the addition of an appropriate surfactant. Examples of known lubricant bases useful in the compositions of this invention include organic oils and greases well known to those skilled in the art. When the phosphaźenes of the present invention are used as additives to conventional, compatible base stocks, it is preferred that the base stocks are polyglycols, polyphenyl ethers and polyol esters. It is more preferred that the base stocks are polyphenyl ethers such as 5P4E which is a polyphenyl ether having five phenyl groups and four ether linkages. Other preferred base stocks include polyol esters such as pentaerythritol tetra $C_{5-9}$ esters (PET).

The lubricant compositions of this invention comprise from about 0.1 to about 100 weight percent of the phosphazenes of the invention. That is, the phosphazenes of this invention may be used as a lubricant base stock (i.e., lubricant composition is up to about 100 weight percent phosphazene) or they may be used as additives with other lubricants (i.e., lubricant composition contains at least about 0.1 weight percent phosphazene).

When the phosphazenes of this invention are used as lubricant additives, it is preferred that they are used in amounts of at least about 0.5 weight percent, more preferably at least about 5 weight percent. It is also preferred that the phosphazenes of the present invention, when used as additives, are used in amounts of no greater than about 50 weight percent, preferably no greater than about 20 weight percent.

As discussed above, the phosphazenes of the present invention may be used as lubricants themselves, either alone or with the addition of additives known in the art. When used as the lubricant base stock, additives useful in high temperature lubricants may be added. In this context, it is preferred that the phosphazene of this invention comprise at least about 50 weight percent, more preferably at least about 95 weight percent of the composition with one or more additives making up the remainder of the lubricant composition. Additionally, the phosphazenes of this invention may be blended with other base stocks to prepare lubricants.

The following examples are provided for illustrative purposes only and should not be construed as limiting the invention in any way. Unless stated otherwise, all parts and percentages are by weight.

EXAMPLE 1

Preparation of
2,2,4,4,6,6-di(4-fluorophenoxy)-tetra(3-trifluoromethylphenoxy)-1,3,5-triaza-2,4,6-triphosphorine A 5.6-g (0.05 mole) portion of 4-fluorophenol and 16.2 g (0.1 mole) 3-trifluoromethylphenol are placed into a flask with 100 ml of toluene and 150 ml of xylene. The flask is equipped with a stirrer and a Dean-Stark trap and 9.6 g (0.15) of potassium hydroxide are added. The mixture is stirred at reflux until waters of reaction cease to evolve. The mixture is then allowed to cool to 100° C. and 8.7 g (0.025 moles) of 2,2,4,4,6,6-hexachloro-1,3,5-triaza-2,4,6-triphosphazene are added in portions as a solid at such a rate to prevent the solvent from distilling from the flask. After this the mixture is refluxed for 16 hours. After cooling, the product is stirred with 1 liter of dilute NaOH water solution, separated and then stirred with 1 liter of water. The product phase is separated, dried over sodium sulfate, filtered and low boilers distilled and saved. The product, 2,2,4,4,6,6-di(4-fluorophenoxy)-tetra(3-trifluoromethylphenoxy)-1,3,5-triaza-2,4,6-triphosphorine, is further distilled at 250° C. and 0.1 mm Hg to produce an oil with a pour point at −10° C. and a thermal stability of 429° C. by DSC.

EXAMPLE 2

Following the procedure outlined in Example 1, 2,2,4,4,6,6-di(2-fluorophenoxy)tetra(3-trifluoromethylphenoxy)-1,3,5-triaza-2,4,6-triphosphorine; 2,2,4,4,6,6-di(3-fluorophenoxy)tetra(3-trifluoromethylphenoxy)-1,3,5-triaza-2,4,6-triphosphorine; 2,2,4,4,6,6,8,8-2.57(4-fluorophenoxy)-5.43(3-trifluoromethylphenoxy)-1,3,5,7-tetraza-2,4,6,8-tetraphosphorine; and 2,2,4,4,6,6,8,8-tri(4-fluorophenoxy)penta(3-trifluoromethylphenoxy)-1,3,5,7-tetraza-2,4,6,8-tetraphosphorine are prepared.

EXAMPLE 3

Preparation of mixture of 4/1 mole ratio of
2,2,4,4,6,6-di(2/1 mole ratio of
3-fluorophenoxy/4-fluorophenoxy)tetra(3-trifluoromethylphenoxy)-1,3,5-triaza-2,4,6-triphosphorine and
2,2,4,4,6,6,8,8-2.57(2/1 mole ratio of
3-fluorophenoxy/4-fluorophenoxy)-5.43(3-trifluoromethylphenoxy)-1,3,5,7-tetraza-2,4,6,8-tetraphosphorine A 26.3-g (0.23 mole) portion of a 2/1 mole ratio of 3-fluorophenol/4-fluorophenol and 76 g (0.47 mole) 3-trifluoromethylphenol are placed into a flask with 50 ml of diglyme and 500 ml of xylene. The flask is equipped with a stirrer and a Dean-Stark trap and 46 g (0.7) of potassium hydroxide are added. The mixture is stirred at reflux until waters of reaction cease to evolve. The mixture is then allowed to cool to 100° C. and 27.8 g (0.02 moles) of 2,2,4,4,6,6-hexachloro-1,3,5-triaza- 2,4,6-triphosphazene and 27.8 g (0.08) mole of 2,2,4,4,6,6,8,8-octachloro-1,3,5,7-tetraza-2,4,6,8-tetraphosphazene are added in portions as a solid at such a rate prevent the solvent from distilling from the flask. After this mixture is refluxed for 16 hours. After cooling, the product is stirred with 1 liter of dilute NaOH water solution, separated and then stirred with 1 liter of water. The product phase is separated, dried over sodium sulfate, filtered and low boilers distilled and saved. The product is distilled to produce an oil with a pour point at −18° C. and boiling point of 285° C. at 0.5 mm Hg.

EXAMPLE 4

Friction and Wear Tests

The anti-wear and extreme pressure characteristics of the compounds and compositions of this invention are measured using the four-ball test using a Falex friction and wear tester. In this example, the compounds tested are trimeric cyclic phosphazenes, i.e., 1,3,5-triaza-2,4,6-triphosphorines having the substituents indicated in Table I below. The four-ball bearing balls used in this test are made of AISI E-52100 steel. Test load is 45 Newtons (10 pounds). The test speed is 1200 rpm and each test is run for 1 hour unless noted otherwise. About 60 cubic centimeters of fluid are used for each test. Each test is conducted at 300° C. During each test, the torque as a function of the wear cycles is monitored on a real time data acquisition basis for data analysis to yield the coefficient of friction. Optical microscope pictures of the bearing balls are taken at the test completion and scar diameter is measured from these pictures. The data obtained is shown in Table I below.

TABLE I

| Run | Substituted Phosphazene | Scar Diameter (mm) | Coefficient of Friction |
|---|---|---|---|
| 1 | di(4-FPh)tetra(3-CF$_3$Ph)[1] | 0.505 | 0.028 |
| 2 | di(2-FPh)tetra(3-CF$_3$Ph)[1] | 0.541 | 0.057 |
| 3 | di(3-FPh)tetra(3-CF$_3$Ph)[1] | 0.569 | 0.028 |
| 4 | mono(3-FPh)penta(3-CF$_3$Ph)[1] | 0.56 | 0.056 |
| 5 | tri(3-FPh)tri(3-CF$_3$Ph)[1] | 0.51 | 0.112 |
| 6[2] | hexa(3-CF$_3$Ph)[1] | 0.957 | 0.119 |
| 7[2] | hexa(Ph)[1] | 0.688 | 0.226 |
| 8[2] | di(3-ClPh)tetra(3-CF$_3$Ph)[1] | 0.908 | 0.170 |
| 9[2] | di(Ph)tetra(3-CF$_3$Ph)[1] | 0.991 | 0.170 |

[1]FPh = fluorophenoxy
CF$_3$Ph = trifluoromethylphenoxy
Ph = phenoxy
ClPh = chlorophenoxy
[2]Not an embodiment of the invention.

The data in the above table clearly demonstrates the effectiveness of the compounds of this invention as high temperature lubricants.

EXAMPLE 4

The procedure outlined in Example 3 is followed with the following exceptions. The test load is 135N and the phosphazenes used are both trimeric and tetrameric substituted phosphazenes. The results obtained are shown in Table II below.

TABLE II

| Phosphazene | Scar Diameter (mm) | Coefficient of Friction |
|---|---|---|
| Trimer[1] | 0.64 | 0.09 |
| Tetramer[2] | 0.70 | 0.10 |

[1]2,2,4,4,6,6-di(4-fluorophenoxy)tetra-(3-trifluoromethylphenoxy)-1,3,5-triaza-2,4,6-triphosphorine
[2]2,2,4,4,6,6,8,8-tri(4-fluorophenoxy)penta-(3-trifluoromethylphenoxy)-1,3,5,7-tetraza-2,4,6,8-tetraphosphorine

EXAMPLE 5

Additive Tests

The procedure outlined in Example 4 is followed with the exception that the phosphazene used in each case is di(3-fluorophenoxy)tetra(3-trifluoromethylphenoxy)phosphazene. Further, the phosphazene is used with varying amounts of a polyphenyl ether (5P4E). In this test, the bearing balls used are M-50 steel balls and the test is conducted at a load of 45N (10 lb) and 135N (30 lb). The test is conducted at 300° C. The results obtained are reported in Table III below.

TABLE III

| | Concentration of Phosphazene (Wt %) | Load | | | |
|---|---|---|---|---|---|
| | | 45 N | | 135 N | |
| Run | | Scar Diameter (mm) | Coefficient of Friction | Scar Diameter (mm) | Coefficient of Friction |
| 1 | 0 | 1.651 | 0.226 | >2.8[2] | 0.206 |
| 2 | 1 | 1.060 | 0.229 | >1.74[2] | 0.189 |
| 3 | 5 | 0.587 | 0.129 | >1.76[2] | 0.189 |
| 4 | 10 | 0.674 | 0.136 | 0.656 | 0.146 |
| 5 | 20 | 0.697 | 0.153 | 0.839 | 0.159 |
| 6 | 100 | 0.678 | 0.145 | 0.771 | 0.151 |

[1]Not an example of the invention.
[2]Test stopped after 15 minutes of test run.

The data shown in Table III above demonstrates the effectiveness of the compound of this invention as an additive to improve the properties of known lubricants.

EXAMPLE 6

Additive Tests

The procedure outlined in Example 5 is followed with the exception that the phosphazene used in each case is tri(4-fluorophenoxy)tri(3-trifluoromethylphenoxy)phosphazene. The concentration of the phosphazene is 10 weight percent. At a load of 45N, the wear scar diameter is 0.82 mm and the coefficient of friction is 0.158. At a load of 135N, the wear scar diameter is 0.89 mm and the coefficient of friction is 0.107.

EXAMPLE 7

Additive Test

The procedure outlined in Example 4 is followed with the exception that the phosphazene used in each case is di(3-fluorophenoxy)tetra(3-trifluoromethylphenoxy)phosphazene. Further, the phosphazene is used with varying amounts of pentaerythritol tetra C$_{4-9}$ ester available commercially as Emery PET 2939. In this test, the bearing balls used are 52100 steel balls and the test is conducted at a load of 535N (120 lb). The test is conducted at 200° C. The results obtained are reported in Table IV below.

TABLE IV

| Percent Triaza | Scar Diameter (mm) | Coefficient of Friction |
|---|---|---|
| 0 | 0.99 | 0.096 |
| 1 | 0.43 | 0.056 |
| 5 | 0.42 | 0.060 |
| 10 | 0.48 | 0.046 |
| 15 | 0.46 | 0.054 |
| 20 | 0.51 | 0.072 |
| 100 | 0.78 | 0.106 |

What is claimed is:

1. A cyclic phosphazene completely substituted with (1) fluorinated phenoxy substituents selected from the group consisting of monofluorinated phenoxy, difluorinated phenoxy, trifluorinated phenoxy, tetrafluorinated phenoxy, and pentafluorinated phenoxy and (2) m-perfluoroalkylphenoxy substituents present in a ratio of fluorophenoxy to m-perfluoroalkylphenoxy ranging from about 1:1 to about 1:5.

2. The compound of claim 1 which corresponds to the following formula:

wherein n is 3 through 7, R is individually in each occurrence fluorinated phenoxy or 3-perfluoroalkylphenoxy with the proviso that the ratio of fluorinated phenoxy to m-perfluoroalkylphenoxy ranges from about 1:1 to about 1:5.

3. The compound of claim 2 wherein the ratio of fluorinated phenoxy to m-perfluoroalkylphenoxy is about 1:2.

4. The compound of claim 2 wherein the fluorinated phenoxy substituent is monofluorinated phenoxy.

5. The compound of claim 4 wherein the monofluorinated phenoxy is m-fluorophenoxy.

6. The compound of claim 4 wherein the monofluorinated phenoxy is o-fluorophenoxy.

7. The compound of claim 4 wherein the monofluorinated phenoxy is p-fluorophenoxy.

8. The compound of claim 2 wherein the perfluoroalkylphenoxy substituents are trifluoromethylphenoxy substituents.

9. The compound of claim 2 wherein n is 3.

10. The compound of claim 2 wherein n is 4.

11. The compound of claim 2 which is 2,2,4,4,6,6-di(4-fluorophenoxy)tetra(3-trifluoromethylphenoxy)-1,3,5-triaza-2,4,6-triphosphorine.

12. The compound of claim 2 which is 2,2,4,4,6,6-di(3-fluorophenoxy)tetra(3-trifluoromethylphenoxy)-1,3,5-triaza-2,4,6-triphosphorine.

13. The compound of claim 2 which is 2,2,4,4,6,6-(3-fluorophenoxy)(4-fluorophenoxy)tetra(3-trifluoromethylphenoxy)-1,3,5-triaza-2,4,6-triphosphorine.

14. A compound of claim 4 which is 2,2,4,4,6,6-tri(fluorophenoxy)tri(3-trifluoromethylphenoxy)-1,3,5-triaza-2,4,6-triphosphorine.

15. A compound of claim 4 which is 2,2,4,4,6,6-mono(fluorophenoxy)penta(3-trifluoromethylphenoxy)-1,3,5-triaza-2,4,6-triphosphorine.

* * * * *